US008431367B2

(12) United States Patent
Shuber

(10) Patent No.: US 8,431,367 B2
(45) Date of Patent: *Apr. 30, 2013

(54) DETECTION OF NUCLEIC ACIDS AND PROTEINS

(75) Inventor: Anthony P. Shuber, Mendon, MA (US)

(73) Assignee: Predictive Biosciences Corporation, Lexington, MA (US)

( * ) Notice: Subject to any disclaimer, the term of this patent is extended or adjusted under 35 U.S.C. 154(b) by 160 days.

This patent is subject to a terminal disclaimer.

(21) Appl. No.: 13/161,074

(22) Filed: Jun. 15, 2011

(65) Prior Publication Data

US 2012/0064529 A1 Mar. 15, 2012

Related U.S. Application Data

(63) Continuation-in-part of application No. 12/034,698, filed on Feb. 21, 2008.

(60) Provisional application No. 60/972,507, filed on Sep. 14, 2007.

(51) Int. Cl.
*C12P 19/34* (2006.01)
*C12Q 1/68* (2006.01)

(52) U.S. Cl.
USPC .......................................... 435/91.2; 435/6.1

(58) Field of Classification Search .................. 435/91.2, 435/6.1
See application file for complete search history.

(56) References Cited

U.S. PATENT DOCUMENTS

| | | | |
|---|---|---|---|
| 5,324,634 A | 6/1994 | Zucker | |
| 6,566,101 B1 | 5/2003 | Shuber et al. | |
| 2004/0219509 A1 | 11/2004 | Valkirs et al. | |
| 2005/0214826 A1 | 9/2005 | Mor et al. | |
| 2006/0246495 A1 | 11/2006 | Garrett et al. | |
| 2007/0099239 A1 | 5/2007 | Tabibiazar et al. | |
| 2007/0178504 A1 | 8/2007 | Colpitts et al. | |
| 2007/0254369 A1 | 11/2007 | Grimes et al. | |
| 2009/0047694 A1 | 2/2009 | Shuber | |
| 2009/0075266 A1 | 3/2009 | Shuber | |
| 2009/0197261 A1 | 8/2009 | Lu et al. | |
| 2009/0264306 A1 | 10/2009 | Caldwell et al. | |
| 2010/0047790 A1 | 2/2010 | Southern et al. | |
| 2010/0221716 A1 | 9/2010 | Flusberg et al. | |
| 2010/0233699 A1 | 9/2010 | Nazarenko et al. | |
| 2010/0323912 A1 | 12/2010 | Korlach | |
| 2011/0183320 A1 | 7/2011 | Flusberg et al. | |
| 2011/0223596 A1 | 9/2011 | Woudenberg et al. | |
| 2011/0245086 A1 | 10/2011 | Lapidus et al. | |
| 2011/0262464 A1 | 10/2011 | Chin et al. | |

FOREIGN PATENT DOCUMENTS

| | | |
|---|---|---|
| WO | 2004/059293 | 7/2004 |
| WO | 2004059293 | 7/2004 |
| WO | 2008/103815 | 8/2008 |
| WO | 2008103815 | 8/2008 |
| WO | 2009036288 | 3/2009 |

OTHER PUBLICATIONS

Langerod et al., Breast Cancer Research, 9(3):1-16, 2007.
Oyama, Frontiers in Bioscience, 12:2299-2308, 2007.
McIntosh et al., Biometrics, 58:657-664, 2002.
Mor et al., PNAS, 10(21):7677-7682, 2005.
Pepe et al., Am J Epidemio, 882-890, 2004.
Wagner, Expert Rev. Mol. Diagn. 4(4):503-511, 2004.
International Search Report and Written Opinion from PCT/US2008/054563, mailed Aug. 18, 2008, 8pp.
Supplementary European Search Report for corresponding application EP 08831219, mailed Jul. 26, 2010, 6pp.
Okragly et al., "Elevated Tryptase, Nerve Growth Factor, Neurotrophin-3 and Glial Cell Line-Derived Neurotrophic Factor Levels in the Urine of Interstitial Cystitis and Bladder Cancer Patient," Journal of Urology, Lippincott Williams & Wilkins, Baltimor, MD, vol. 161, No. 2, Feb. 1, 1999, pp. 438-442.
Sheu Chau-Chyun et al., "Combined detection of CEA, CK-19 and c-met mRNAs in peripheral blood: A highly sensitive panel for potential molecular diagnosis of non-small cell lung cancer," Oncology (Basel), vol. 70, No. 3, 2006, pp. 203-211.
Jaeger, et al., Am. Hematol. 82: 139-147, 2003.
Witherspoon, L.R. et al., The Journal of Urology, abstract, 157(4): 1322-1328, 1997.
Hill and Mirken, "The bio-barcode assay for the detection of protein and nucleic acid targets using DTT-induced ligand exchange" Nature Protocols, vol. 1, No. 1. pp. 324-336 (2006).
Shipp, "Ultrasensitive Measurement of Protein and Nucleic Acid Biomarkers for Earlier Disease Detection and More Effective Therapies" Biotechnology Healthcare, pp. 35-40. Apr. 2006.
Yang ang Ellington, "Real-time PCR detection of protein analytes with conformation-switching aptamers" Analytical Biochemistry 380 (2008). pp. 164-173.
Fang, et al. "Synthetic DNA Aptamers to Detect Protein Molecular Variants in a High-Throughput Fluorescence Quenching Assay," ChemBioChem 2003, 4, 829-834.
International Search Report from PCT/US08/76193, mailed Jan. 16, 2009, 2pp.
Written Opinion from PCT/US08/76193, mailed Jan. 16, 2009, 4pp.
International Preliminary Report on Patentability from PCT/US08/76193, mailed Mar. 25, 2010, 5pp.
Supplementary European Search Report for EP 08831219, mailed Jul. 26, 2010, 6pp.

(Continued)

*Primary Examiner* — Cynthia Wilder
(74) *Attorney, Agent, or Firm* — Thomas C. Meyers; Brown Rudnick LLP

(57) ABSTRACT

The invention generally relates to methods for detecting a target nucleic acid and a target protein in a single assay.

21 Claims, No Drawings

OTHER PUBLICATIONS

Okragly et al., "Elevated Tryptase, Nerve Growth Factor, Neurotrophin-3 and Glial Cell Line-Derived Neurotrophic Factor Levels in the Urine of Interstitial Cystitis and Bladder Cancer Patient," Journal of Urology, Lippincott Williams & Wilkins, Baltimore, MD, vol. 161, No. 2, Feb. 1, 1999, pp. 438-442.

Sheu Chau-Chyun et al., "Combined detection of CEA, CK-19, and c-met mRNAs in peripheral blood: A highly sensitive panel for potential molecular diagnosis of non-small cell lung cancer," Oncology (Basel), vol. 70, No. 3, 2006, pp. 203-211.

Jaeger, et al., "Monitoring minimal residual disease in AML: the right time for real time." Am. Hematol. 82: 139-147, 2003.

Witherspoon, L.R. et al., "Sensitive prostate specific antigen measurements identify men with long disease-free intervals and differentiate aggressive from indolent cancer recurrences within 2 years after radical prostatectomy." The Journal of Urology, abstract, 157(4): 1322-1328, 1997.

DETECTION OF NUCLEIC ACIDS AND PROTEINS

RELATED APPLICATION

The present application is a continuation-in-part of U.S. nonprovisional patent application Ser. No. 12/034,698, filed Feb. 21, 2008, which claims the benefit of and priority to U.S. provisional patent application Ser. No. 60/972,507, filed Sep. 14, 2007, the content of each of which is incorporated by reference herein in its entirety.

FIELD OF THE INVENTION

The invention generally relates to methods for detecting a target nucleic acid and a target protein in a single assay.

BACKGROUND

Diagnostic assays based upon multiple biomarkers have been used on only a limited basis. For example, assays have been proposed in which gene expression is measured in several genes in order to assess clinical status. Also, multiple protein analytes have been used to screen for the presence of any of multiple disorders when diagnosis is unclear. Generally, algorithms are used in order to assess the results of any standard assay and, in particular to assess whether additional testing is needed. However, since different biomarker types provide different informative results, most assays have been limited to a single marker or analyte per condition to be screened.

It is common to screen multiple analytes from the same sample for different clinical indications. This is especially true when a patient presents with ambiguous symptoms. For example, a single blood sample may be screened for hematocrit, hepatitis antigen, HIV, and SARS. Each of those screens, however, is directed to a different clinical condition and is tied into a different algorithm to produce separate results for each of the clinical indications that the marker is intended to measure. Such a broad screen is used to rule out or rule in one or more diagnostic pathways in a situation in which diagnosis is ambiguous or difficult.

Increasing the number of biomarkers in any screening assay increases the accuracy of diagnosis. However, there is no assay that allows the screening and/or diagnosis of a condition based upon a plurality of biomarkers. Therefore, there is a need in the art for assays and diagnostic algorithms that allow screening and diagnosis of a condition based upon multiple biomarkers.

SUMMARY

The invention provides methods for assessing the clinical status of a patient. In particular, the invention provides methods for creating a diagnostic readout based upon analysis of multiple analytes or biomarkers. In practice, methods of the invention provide the ability to screen patients based upon a plurality of biomarkers in a single assay format.

Methods of the invention are particularly useful in complex diagnostic assessment. The invention allows multiplex analysis of a plurality of biomarkers in order to increase the diagnostic power and accuracy of the result. According to one aspect of the invention, a plurality of different biomarkers obtained from a patient sample are assessed. The results are then normalized and a diagnostic score is produced based upon the normalized biomarker data. In a preferred embodiment, levels of each of a plurality of biomarkers in a patient sample are obtained. Each biomarker is then assigned a binary result (e.g., a 1 or a 0) based upon whether the detected level of the biomarker in the patient sample exceeds a predetermined threshold. Then, a cumulative score is obtained by adding the binary results in order to produce a diagnostic score that is used in clinical evaluation. In another preferred embodiment, biomarker results are weighted based upon known diagnostic criteria and/or patient history, lifestyle, symptoms, and the like. The resulting aggregate weighted score is used for clinical assessment.

In certain embodiments of the invention, the readout of the plurality of biomarkers need not be binary. Rather, the readout may take into consideration the predictive value of each of the biomarkers for the condition being assessed. This is a form of weighting based upon known risk factors, diagnostic criteria, and patient history and can be tuned to reflect the degree of confidence that one expects from the assay. Methods of the invention allow the generation of a signature based upon results obtained from a plurality of biomarkers, wherein the signature is indicative of the presence/absence of disease, the stage of disease, or prognostic factors (such as likelihood of recurrence, assessment of response to treatment, and risk of developing disease).

Methods of the invention make use of the measurement of numerous different markers that have a predictive relationship or possible predictive value in diagnosis, prognosis, therapeutic selection, therapeutic efficacy, physiological trait, and/or the likelihood of recurrence. The predictive power of multiplex diagnostic assessment creates a significant advantage in terms of both the specificity and sensitivity of the assay. The predictive power of the assay resides in its ability to take results from a number of different markers and combine them into a single diagnostic signature or result that encompasses the predictive power of each of the individual markers in order to produce a highly-sensitive, highly-specific result.

Accordingly, in one embodiment of the invention, a plurality of biomarkers are measured in a sample obtained from a patient. The plurality of biomarkers are selected from proteins (including antibodies, enzymes, etc.), nucleic acids, carbohydrates, sugars, bacteria, viruses, pH, acids, bases, vitamins, ions, hormones, and drugs. In some cases, for example in the case of nucleic acids and proteins, expression levels may be measured over time. In other cases, levels of a biomarker are obtained in whatever units may be appropriate for that biomarker. Levels can optionally then be normalized across an entire panel of biomarkers or can be assigned a binary result based upon whether a threshold is exceeded or not.

In some embodiments, results of a panel of biomarkers are used in diagnostic screening as they are obtained from an individual assay of the various biomarkers. In other cases, normalization occurs prior to diagnostic determination, and in still other cases, biomarker results are simply assigned a binary unit (e.g., a 1 or a 0). Cumulative results are then assessed based upon cumulative binary input (i.e., the sum of all 1s and 0s) or on the basis of weighted averages or on the basis of a signature generated by the panel of markers chosen.

Markers chosen for multiplex diagnostic assays of the invention are chosen based upon their predictive value or suspected predictive value for the condition or conditions being diagnosed. Particular markers are selected based upon various diagnostic criteria, such as suspected association with disease. The number of markers chosen is at the discretion of the user and depends upon the cumulative predictive ability of the markers and the specificity/sensitivity of individual markers in the panel. A panel of markers can be chosen to increase the effectiveness of diagnosis, prognosis, treatment response, and/or recurrence. In addition to general concerns around specificity and sensitivity, markers can also be chosen in consideration of the patient's history and lifestyle. For example, other diseases that the patient has, might have, or has had can effect the choice of the panel of biomarkers to be analyzed. Drugs that the patient has in his/her system may also affect panel selection.

The invention is applicable to diagnosis and monitoring of any disease, either in symptomatic or asymptomatic patient populations. For example, the invention can be used for diagnosis of infectious diseases, inherited diseases, and other conditions, such as disease or damage caused by drug or alcohol abuse. The invention can also be applied to assess therapeutic efficacy, potential for disease recurrence or spread (e.g. metastisis).

The invention is especially useful in screening for cancer. Examples of biomarkers associated with cancer include matrix metalloproteinase (MMP), neutrophil gelatinase-associated lipocalin (NGAL), MMP/NGAL complex, thymosin β4, thymosin β10 thymosin β15, collagen like gene (CLG) product, prohibitin, glutathione-S-transferase, beta-5-tubulin, ubiquitin, tropomyosin, Cyr61, cystatin B, chaperonin 10, and profilin. Examples of MMPs include, but are not limited to, MMP-2, MMP-9, MMP9/NGAL complex, MMP/TIMP complex, MMP/TIMP1 complex, ADAMTS-7 or ADAM-12, among others. Also, the patient sample from which a biomarker is obtained is immaterial to the functioning of the invention. Preferred sample sources include blood, serum, sputum, stool, saliva, urine, cerebral spinal fluid, breast nipple aspirate, and pus.

Methods of the invention can be used on patients known to have a disease, or can be used to screen healthy subjects on a periodic basis. A subject can be screened for one or more diseases simultaneously using methods of the invention. Screening can be done on a regular basis (e.g., weekly, monthly, annually, or other time interval); or as a one time event. The outcome of the analysis may be used to alter the frequency and/or type of screening, diagnostic and/or treatment protocols. Different conditions can be screened for at different time intervals and as a function of different risk factors (e.g., age, weight, gender, history of smoking, family history, genetic risks, exposure to toxins and/or carcinogens etc., or a combination thereof). The particular screening regimen and choice of markers used in connection with the invention are determined at the discretion of the physician or technician.

Threshold values for any particular biomarker and associated disease are determined by reference to literature or standard of care criteria or may be determined empirically. In a preferred embodiment of the invention, thresholds for use in association with biomarker panels of the invention are based upon positive and negative predictive values associated with threshold levels of the marker. In one example, markers are chosen that provide 100% negative predictive value, in other words patients having values of a sufficient number of markers (which may be only one) below assigned threshold values are not expected to have the disease for which the screen is being conducted and can unambiguously be determined not to need further intervention at that time. Conversely, threshold values can be set so as to achieve approximately 100% positive predictive value. In that case, a critical number of biomarker levels above that threshold are unambiguously associated with the need for further intervention. As will be apparent to the skilled artisan, for certain biomarkers positive and negative predictive values do not have to be 100%, but can be something less than that depending upon other factors, such as the patients genetic history or predisposition, overall health, the presence or absence of other markers for diseases, etc.

Further aspects and features of the invention will be apparent upon inspection of the following detailed description thereof.

DETAILED DESCRIPTION

The invention provides methods for clinical assessment in which a panel of different biomarkers obtained from a patient tissue or body fluid sample are analyzed and aggregated to produce a clinically-informative result. The result of using methods of the invention is increased diagnostic range and power.

According to the invention, multiple biomarkers are obtained from a patient sample (e.g., tissue or body fluid samples). Levels of the various markers are appropriately determined and a cumulative diagnostic/prognostic result is produced. Any number of different biomarkers can be chosen based upon the condition or conditions being screened. In many instances as, for example, in cancer, nucleic acid mutations, expression levels, methylation patterns and the like are screened in coordination with protein levels. In an alternative example, steroid or protein hormones can be screened in conjunction with other types of markers and an aggregate diagnostic "score" can be produced. Other combinations of markers are apparent to those of ordinary skill in the art and will depend upon the disease or condition for which screening is being conducted.

The invention allows the use of different analytes or biomarkers in a single diagnostic algorithm in order to increase predictive power. According to the invention, multiple analytes are measured and the measured outputs are converted into a single readout score or a signature that is predictive of clinical outcome. The readout can be binary (e.g., 1/0, yes/no) or can be a point on a continuum that represents a degree of risk of disease or severity or likely outcome (e.g., of treatment, recurrence, etc.). In any of these cases, the readout is correlated to predictive outcomes at a desired level of confidence. For example, upon analysis of multiple analytes, a signature can be generated based upon the pattern of results obtained for the selected panel. That signature is then correlated to clinical outcome based upon comparison to a training set with the same panel or empirically based upon prior results. The determination of individual analyte results can also be placed into a bar code format that can be structured to correlate with clinical outcome. Individual assay results can either be weighted or not and can either be normalized or not depending upon the needs of the overall result.

By way of example, one aspect the invention provides a binary algorithm in which DNA and protein measurements are made in order to provide a diagnostic readout. In this example, an assay is conducted to determine whether a mutation exists in a genomic region known to associate with cancer. For example, a single nucleotide polymorphism known to be predictive of disease onset is first determined. There are numerous means for doing this, such as single base extension assays (e.g., U.S. Pat. No. 6,566,101, incorporated by reference herein). A result indicating whether the mutation is present or not (1 or 0) is obtained. Several other DNA mutations can be measured as well and similarly assigned a binary score for disease association. As many mutation-based assays as are desired can be performed. The level of a protein or proteins known to be informative for cancer is also measured. This could be, for example, the tumor suppressor p53. It is determined whether the level of that protein exceeds a threshold amount known to be indicative of the presence of disease. A binary result is also assigned to this analyte (e.g., 1 if threshold is exceeded and 0 if it is not). Finally, a quantitative RNA assay is performed to determine the level or levels of diagnostically-relevant RNA expressed in the sample. A binary result is obtained based upon the expression levels obtained for each RNA species measured, and comparison to known disease-associated thresholds. The result of all these assays is a series of binary outcomes that form a barcode-type readout that is assigned clinical status based upon a priori determinations of disease association for the entire marker panel.

In another aspect of the invention, each of the assayed biomarkers produces a quantitative result that is also assigned a weighted value based upon how much of the analyte is present in the sample relative to a predetermined threshold for the marker. For each marker, a result above the cutoff is given a weighted positive score (in this case based upon amount present in excess of the cutoff) and those below the threshold are given a weighted negative score. The weighted scores are then assessed to provide an overall diagnostic readout.

There are numerous methods for determining thresholds for use in the invention, including reference to standard values in the literature or associated standards of care. The precise thresholds chosen are immaterial as long as they have the desired association with diagnostic output.

Similarly, the biomarker chosen is immaterial to the operation of the invention as long as the marker is associated with the disease for which screening is being conducted. Some biomarkers that have been associated with disease include nucleic acid markers (including but not limited to K-ras, K-ras2, APC, DCC, TP53, PRC I, NUSAPI, CAPZ, PFKP, EVER1, FLT1, ESPL I, AKAP2, CDC45L, RAMP, SYNGR2, NDRG1, ZNF533, and hypermethylated nucleic acid), proteins and peptides, carbohydrates, sugars, glycans, lipids, hormones (e.g., antidiuretic hormone (ADH), Adrenocorticotrophic hormone (ACTH), growth hormone(GH), follicle stimulating hormone (FSH), luteinizing hormone (LH), estrogen (estradiol, estrone, estriol), progesterone, testosterone, dihydrotestosterone (DHT), inhibin, somatotropin, dehydroepiandrostenedione (DHEA), somatostatin, glucagon, insulin, thyrotropin, thyroid stimulating hormone (TSH), thyroxin, parathyroid hormone, corticotropin, cortisol, corticosteron, aldosterone, epinephrine, norepinephrine, prolactin, vasopressin, oxytocin, melanocyte stimulating hormone (MSH)), growth factors (e.g., granulocyte-colony stimulating factor (G-CSF), granulocyte-macrophage colony stimulating factor (GM-CSF), nerve growth factor (NGF), neurotrophins, platelet-derived growth factor (PDGF), erythropoeitin (EPO), thrmobopoeitin (TPO), myostatin (GDF-8), growth differentiation factor (GDF-9), basic fibroblast growth factor (bFGF or FGF2), acidic fibroblast growth factor, fibroblast growth factor receptor 3 (FGFR3), epidermal growth factor (EGF), hepatocyte growth factor (HGF), human stem cell factor (SCF), tumor necrosis factor (TNF), tumor necrosis factor-β (TNF-β), tumor necrosis factor-α (TNF-α), vascular endothelial growth factor (VEGF), transforming growth factor-β (TGF-β), transforming growth factor-α (TGF-α), insulin-like growth factor-I (IGF-II), insulin-like growth factor-II (IGF-II), and colony stimulating factor (CSF)), cytokines (e.g., IL-1α, IL-1β, IL-2, IL-3, IL-4, IL-5, IL-6, IL-7, IL-8, IL-9, IL-10, IL-11, IL-12, IL-13, IFN-α, IFN-β, and IFN-γ), proteins (e.g., Matrix metalloproteinases (MMPs) such as MMP2, MMP9, neutrophil gelatinase-associated lipocalin (NGAL), MMP/NGAL complex, thymosin β15, thymosin β16, collagen like gene (CLG) product, prohibitin, glutathione-S-transferase, beta-5-tubulin, ubiquitin, tropomyosin, Cyr61, cystatin B, chaperonin 10, profilin, Alpha-fetoprotein, Carcinoembryonic antigen, Epidermal growth factor receptor, Kallikrein 3 (prostate specific antigen), Vascular endothelial growth factor A, VEGF, Albumin, CA 125, Calcitonin, Chromogranin A (parathyroid secretory protein 1), Corticotropin-lipotropin contains ACTH, Estrogen receptor 1, Gastrin, Progesterone receptor, Prolactin, S100 alpha chain, Somatostatin, Thyroglobulin, V-erb-b2, Her2/neu, Antigen identified by monoclonal antibody Ki-67, B-cell CLUlymphoma 2, BCL2-associated X protein, Beta-2-microglobulin, Breast cancer 1 early onset, BRCA1, CA 15.3, CA 19.9, Cadherin 1 type 1 E-cadherin (epithelial), Caspase 3, CD44 antigen, Cellular tumor antigen p53, Coagulation factor II, prothrombin, Colony stimulating factor 2 (granulocyte-macrophage), Colony stimulating factor 3 (granulocyte), C-reactive protein, Cyclin D1, Cyclin-dependent kinase inhibitor 1, p21, Erythropoietin, Fibrinogen alpha/alpha-E chain, Follicle-stimulating hormone, Gamma enolase, Insulin, Interferon gamma, Interleukin 2, Interleukin 6, k-ras, Neprilysin, CD10, Transferrin, Trypsin, Tumor necrosis factor (TNF-alpha), Tumor necrosis factor receptor superfamily member 6, fas, Von Willebrand Factor, Chemokine, Chitinase-3 like protein 1, YKL-40, Choriogonadotropin beta chain, Colony stimulating factor 1 (macrophage), Haptoglobin-1, Hepatocyte growth factor, Inhibin, Interferon-alpha/beta receptor alpha chain, Interferon-alpha/beta receptor beta chain, Kallikrein 10, Kallikrein 11, Kallikrein 6, Matrix metalloproteinase 3, ADAM-12, Small inducible cytokine A21 (CCL21) soluble IL-2R alpha, Somatotropin growth factor, growth hormone, Breast cancer 2 early onset, BRCA2, Catenin Beta 1, Cathepsin D, CD15, Desmin, DNA-(apurinic or apyrimidinic site) lyase, APEX, Lutropin beta chain, Luteinizing hormone, Parathyroid Hormone, Proliferating cell nuclear antigen, Tumor necrosis factor ligand superfamily member 8 (CD30 ligand), V-myc myelocytomatosis viral oncogene homolog (avian), Tumor necrosis factor ligand superfamily member 8 (CD30), 17beta-Hydroxysteroid dehydrogenase type 1 (17HSD1), Acid phosphatase prostate, Adrenomedullin, Aldolase A, bone-specific Alkaline phosphatase, Alkaline phosphatase, placental type, Alpha-1-acid glycoprotein 1, orosomucoid, Alpha-1-antitrypsin, alpha-2-H S-glycoprotein, Alpha-2-macroglobulin, Alpha-lactalbumin, Angiogenin ribonuclease RNase A family 5, Angiopoietin 1, Angiopoietin 2, Antileukoproteinase 1, SLPI, Apolipoprotein A1, Apolipoprotein A-II, Apolipoprotein C-1, Apolipoprotein C-III, Bone sialoprotein II, Brain-derived neurotrophic factor, Breast cancer metastasis-suppressor 1, CA 27.29, CA 72-4, Cathepsin B, CC chemokine 4, HCC-4, CD44 variant V5 soluble, Ceruloplasmin, Cervical cancer 1 protooncogene protein p40, Chemokine (C-C motif) ligand 4 Small inducible cytokine A4 (CCL4), MIP-1-beta, Claudin-3, Claudin-4, Clusterin, Coagulation factor III, Coagulation factor XIII A chain, Coagulation factor XIII B chain, Collagen I c-terminal telopeptide, Complement component 3, Complement component 4, Complement component 7, Complement factor H related protein, Cyclin-dependent kinase 6, Cyclooxygenase-2, Cystatin A, Cystatin B, Cystatin C, Cytokeratin 8, Diazepam binding inhibitor, Endoglin, Endothelin 1, Epidermal growth factor, E-selectin, Ferritin H, Fibroblast growth factor 2 (basic), Fibronectin 1, Flt-3 ligand, Fms-related tyrosine kinase 1, VEGFRI, Follistatin, Fructose-bisphosphate aldolase B, Fructose-bisphosphate aldolase C, Geminin, Glucose-6-phosphate isomerase, Glypican-3, n-terminal, Growth arrest and DNA-damage-inducible alpha, Immunosuppressive acidic protein, Insulin-like growth factor 1 (somatomedin C), Insulin-like growth factor 2 (somatomedin A), Insulin-like growth factor binding protein 1, Insulin-like growth factor binding protein 2, Insulin-like growth factor binding protein 3, Intercellular Adhesion Molecule 1, Interferon alpha 1, Interleukin 1 alpha, Interleukin 1 beta, Interleukin 10, Interleukin 12A, Interleukin 16, Interleukin 5, Interleukin 6 receptor, Interleukin 6 signal transducer, Interleukin 7, Interleukin 8, Interleukin 9, Interleukin-1 receptor antagonist protein, IRAP, Kallikrein 14 (hK14), Kallikrein 2 prostatic, Kallikrein 5, Kallikrein 7, Kallikrein 8, Kallikrein 18, Kallikrein 8, Keratin 18, Keratin, type I cytoskeletal 19, cytokeratin 19, Kit ligand, Lactotransferrin, Leptin, L-selectin, Luteinizing hormone-releasing hormone receptor, Mac-2 Binding Protein 90K, Mammaglobin B, Mammary Serum, Antigen, Mast/stem cell growth factor receptor, Melanoma-inhibiting activity, Membrane cofactor protein, CD46 antigen, Mesothelin, Midkine, MK-1 protein, Ep-CAM, Myoblast determination protein 1, Nerve growth factor beta, Netrin-1, Neuroendocrine secretory protein-55, Neutrophil defensin 1, Neutrophil defensin 3, Nm23-H 1, OVX1, OX40, p65 oncofetal protein, Pancreatic secretory trypsin inhibitor, TATI, Parathyroid hormone-related protein, Pcaf, P300/CBP-associated factor, Pepsinogen-1, Placental specific tissue protein 12 Plasma retinol-binding protein, Plasminogen (Contains Angiostatin), Platelet endothelial cell adhesion molecule, PECAM-1, Platelet factor 4, Platelet-derived growth factor beta polypeptide, Platelet-derived growth factor receptor alpha polypeptide, Pregnancy zone protein, Pregnancy-associated plasma protein-A, Prostate secretory protein PSP94, P-selectin, PSP94 binding protein, Pyruvate kinase, isozymes M1/ M2, Riboflavin carrier protein, 100 beta chain, Secreted phosphoprotein 1, osteopontin, Serine (or cysteine) proteinase inhibitor Glade B, maspin, Serine (or cysteine) proteinase inhibitor clade E, PAI-1, Serum amyloid alpha-1, Serum paraoxonase/arylesterase 1, Small inducible cytokine A14 CCL14, Small inducible cytokine A18(CCL18), MIP-4, Small inducible cytokine A2(CCL2), Small inducible cytokine A3(CCL3), Macrophage inflammatory protein 1-alpha, Small inducible cytokine B5(CXCL5), Squamous cell carcinoma antigen 1, Squamous cell carcinoma antigen 2, Survivin, Syndecan-1, synuclein-gamma, TEK tyrosine kinase endothelial, Tie-2, Tenascin, Tetranectin, TGF-beta receptor type III, Thiredoxin reductase 1, Thrombopoietin, Thrombopoietin 1, Thymidin kinase, Tissue inhibitor of metalloproteinasel, Tissue inhibitor of metalloproteinase2, Tissue-type plasminogen activator, tPA, Transferrin receptor (p90 CD71), Transforming growth factor alpha, Transforming growth factor beta 1, transthyretin, Tropomyosin 1 alpha chain (Alpha-tropomyosin), Tumor necrosis factor (ligand) superfamily member 5, CD154, Tumor necrosis factor (ligand) superfamily member 6, Fas ligand, Tumor necrosis factor ligand superfamily member 13B, TALL-1, Tumor necrosis factor receptor superfamily member 11 B, osteoprotegerin, Tumor necrosis factor receptor superfamily member 1A p60 TNF-RI p55 CD120a, TNFR1, Tumor necrosis factor receptor superfamily member 1B, TNFR2, Urokinase plasminogen activator surface receptor, U-PAR, Vascular cell adhesion molecule 1, Vascular endothelial growth factor receptor 2, Vasoactive intestinal peptide, VEGF(165)b, Vitamin K dependent protein C, Vitronectin, and X box binding protein-1), antibodies, or any combination thereof.

In another aspect of the invention, a single assay is used to detect both nucleic acids and proteins from a single sample. Biological samples usually do not include a sufficient amount of DNA for detection. A common technique used to increase the amount of nucleic acid in a sample is to perform PCR on the sample prior to performing an assay that detects the nucleic acids in the sample. PCR involves thermal cycling, consisting of cycles of repeated heating and cooling of a reaction for DNA melting and enzymatic replication of the DNA. Most PCR protocols involve heating DNA to denature the double stranded DNA in the sample, cooling the DNA to allow for annealing of primers to the single-stranded DNA to form DNA/primer complexes and binding of a DNA polymerase to the DNA/primer complexes, and re-heating the sample so that the DNA polymerase synthesizes a new DNA strand complementary to the single-stranded DNA. This process amplifies the DNA in the sample and produces an amount of DNA sufficient for detection by standard assays known in the art, such as Southern blots or sequencing.

A problem with detecting both nucleic acids and proteins in a single assay is that the temperatures used for PCR adversely affect proteins in the sample, making the proteins undetectable by methods known in the art, such as western blots. For example, the required heating step in a PCR reaction brings the sample to a temperature that can result in irreversible denaturation of proteins in the sample and/or precipitation of proteins from the sample. Additionally, thermal cycling, i.e., repeated heating and cooling, can cause proteins in a sample to adopt a non-native tertiary structure. Once denatured, the proteins usually cannot be detected by standard protein assays such as western blots, immunoprecipitation, or immunoelectrophoresis. Therefore a need exists for a single assay that can analyze both proteins and nucleic acids in a sample.

Methods of the present invention can detect a target nucleic acid and a target protein in a single assay. In certain embodiments, methods of the invention are accomplished by adding an aptamer to a sample that binds a target protein in the sample to form an aptamer/protein complex. An aptamer (nucleic acid ligand) is a nucleic acid macromolecule (e.g. DNA or RNA) that binds tightly to a specific molecular target, such as a protein. Since an aptamer is composed of DNA or RNA, it can be PCR amplified and can be detected by standard nucleic acid assays. PCR may then be used to amplify the nucleic acids and the aptamer in the sample. The amplified nucleic acids and aptamer may then be detected using standard techniques for detecting nucleic acids that are known in the art. In particular embodiments, the detection method is sequencing. Detection of the aptamer in the sample indicates the presence of the target protein in the sample.

As used herein, "aptamer" and "nucleic acid ligand" are used interchangeably to refer to a nucleic acid that has a specific binding affinity for a target molecule, such as a protein. Like all nucleic acids, a particular nucleic acid ligand may be described by a linear sequence of nucleotides (A, U, T, C and G), typically 15-40 nucleotides long. Nucleic acid ligands can be engineered to encode for the complementary sequence of a target protein known to associate with the presence or absence of a specific disease.

In solution, the chain of nucleotides form intramolecular interactions that fold the molecule into a complex three-dimensional shape. The shape of the nucleic acid ligand allows it to bind tightly against the surface of its target molecule. In addition to exhibiting remarkable specificity, nucleic acid ligands generally bind their targets with very high affinity, e.g., the majority of anti-protein nucleic acid ligands have equilibrium dissociation constants in the picomolar to low nanomolar range.

Aptamers used in the methods of the invention depend upon the target protein to be detected. Nucleic acid ligands for specific target proteins may be discovered by any method known in the art. In one embodiment, nucleic acid ligands are discovered using an in vitro selection process referred to as SELEX (Systematic Evolution of Ligands by Exponential enrichment). See for example Gold et al. (U.S. Pat. Nos. 5,270,163 and 5,475,096), the contents of each of which are herein incorporated by reference in their entirety. SELEX is an iterative process used to identify a nucleic acid ligand to a chosen molecular target from a large pool of nucleic acids. The process relies on standard molecular biological techniques, using multiple rounds of selection, partitioning, and amplification of nucleic acid ligands to resolve the nucleic acid ligands with the highest affinity for a target molecule. The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. There have been numerous improvements to the basic SELEX method, any of which may be used to discover nucleic acid ligands for use in methods of the invention.

In methods of the invention, aptamers are introduced to the sample to bind the target protein. Certain of the aptamers bind the protein(s) of interest in the sample to form aptamer/protein complexes. The unbound aptamers are then separated and/or removed from sample using standard methods known in the art. See for example, Schneider et al., U.S. Patent Application Publication Number 2009/0042206, the content of which is incorporated by reference herein in its entirety.

Amplification refers to production of additional copies of a nucleic acid sequence. See for example, Dieffenbach and Dveksler, PCR Primer, a Laboratory Manual, Cold Spring Harbor Press, Plainview, N.Y. (1995), the contents of which is hereby incorporated by reference in its entirety. The amplification reaction may be any amplification reaction known in the art that amplifies nucleic acid molecules, such as polymerase chain reaction, nested polymerase chain reaction, polymerase chain reaction-single strand conformation polymorphism, ligase chain reaction, strand displacement amplification and restriction fragments length polymorphism.

In certain methods of the invention, the target nucleic acid and the nucleic acid ligand are PCR amplified. PCR refers to methods by K. B. Mullis (U.S. Pat. Nos. 4,683,195 and 4,683, 202, hereby incorporated by reference) for increasing concentration of a segment of a target sequence in a mixture of genomic DNA without cloning or purification. The process for amplifying the target nucleic acid sequence and nucleic acid ligand includes introducing an excess of oligonucleotide primers that bind the nucleic acid and the nucleic acid ligand, followed by a precise sequence of thermal cycling in the presence of a DNA polymerase. The primers are complementary to their respective strands of the target nucleic acid and nucleic acid ligand.

To effect amplification, the mixture of primers are annealed to their complementary sequences within the target nucleic acid and nucleic acid ligand. Following annealing, the primers are extended with a polymerase so as to form a new pair of complementary strands. The steps of denaturation, primer annealing and polymerase extension can be repeated many times (i.e., denaturation, annealing, and extension constitute one cycle; there can be numerous cycles) to obtain a high concentration of an amplified segment of a desired target and nucleic acid ligand. The length of the amplified segment of the desired target and nucleic acid ligand is determined by relative positions of the primers with respect to each other, and therefore, this length is a controllable parameter.

With PCR, it is possible to amplify a single copy of a specific target sequence in genomic DNA to a level that can be detected by several different methodologies (e.g., staining, hybridization with a labeled probe, incorporation of biotinylated primers followed by avidin-enzyme conjugate detection, incorporation of 32P-labeled deoxynucleotide triphosphates, such as dCTP or dATP, into the amplified segment).

In one embodiment of the invention, the target nucleic acid and nucleic acid ligand can be detected using detectably labeled probes. Nucleic acid probe design and methods of synthesizing oligonucleotide probes are known in the art. See, e.g., Sambrook et al., DNA microarray: A Molecular Cloning Manual, Cold Spring Harbor, N.Y., (2003) or Maniatis, et al., Molecular Cloning: A Laboratory Manual, Cold Spring Harbor, N.Y., (1982), the contents of each of which are herein incorporated by reference herein in their entirety. Sambrook et al., Molecular Cloning: A Laboratory Manual ($2^{nd}$ Ed.), Vols. 1-3, Cold Spring Harbor Laboratory, (1989) or F. Ausubel et al., Current Protocols In Molecular Biology, Greene Publishing and Wiley-Interscience, New York (1987), the contents of each of which are herein incorporated by reference in their entirety. Suitable methods for synthesizing oligonucleotide probes are also described in Caruthers, Science, 230:281-285, (1985), the contents of which are incorporated by reference.

Probes suitable for use in the present invention include those formed from nucleic acids, such as RNA and/or DNA, nucleic acid analogs, locked nucleic acids, modified nucleic acids, and chimeric probes of a mixed class including a nucleic acid with another organic component such as peptide nucleic acids. Probes can be single stranded or double stranded. Exemplary nucleotide analogs include phosphate esters of deoxyadenosine, deoxycytidine, deoxyguanosine, deoxythymidine, adenosine, cytidine, guanosine, and uridine. Other examples of non-natural nucleotides include a xanthine or hypoxanthine; 5-bromouracil, 2-aminopurine, deoxyinosine, or methylated cytosine, such as 5-methylcytosine, and N4-methoxydeoxycytosine. Also included are bases of polynucleotide mimetics, such as methylated nucleic acids, e.g., 2'-O-methRNA, peptide nucleic acids, modified peptide nucleic acids, and any other structural moiety that can act substantially like a nucleotide or base, for example, by exhibiting base-complementarity with one or more bases that occur in DNA or RNA.

The length of the nucleotide probe is not critical, as long as the probes are capable of hybridizing to the target nucleic acid and nucleic acid ligand. In fact, probes may be of any length. For example, probes may be as few as 5 nucleotides, or as much as 5000 nucleotides. Exemplary probes are 5-mers, 10-mers, 15-mers, 20-mers, 25-mers, 50-mers, 100-mers, 200-mers, 500-mers, 1000-mers, 3000-mers, or 5000-mers. Methods for determining an optimal probe length are known in the art. See, e.g., Shuber, U.S. Pat. No. 5,888,778, hereby incorporated by reference in its entirety.

Probes used for detection may include a detectable label, such as a radiolabel, fluorescent label, or enzymatic label. See for example Lancaster et al., U.S. Pat. No. 5,869,717, hereby incorporated by reference. In certain embodiments, the probe is fluorescently labeled. Fluorescently labeled nucleotides may be produced by various techniques, such as those described in Kambara et al., Bio/Technol., 6:816-21, (1988); Smith et al., Nucl. Acid Res., 13:2399-2412, (1985); and Smith et al., Nature, 321: 674-679, (1986), the contents of each of which are herein incorporated by reference in their entirety. The fluorescent dye may be linked to the deoxyribose by a linker arm that is easily cleaved by chemical or enzymatic means. There are numerous linkers and methods for attaching labels to nucleotides, as shown in Oligonucleotides and Analogues: A Practical Approach, IRL Press, Oxford, (1991); Zuckerman et al., Polynucleotides Res., 15: 5305-5321, (1987); Sharma et al., Polynucleotides Res., 19:3019, (1991); Giusti et al., PCR Methods and Applications, 2:223-227, (1993); Fung et al. (U.S. Patent Number 4,757,141); Stabinsky (U.S. Patent Number 4,739,044); Agrawal et al., Tetrahedron Letters, 31:1543-1546, (1990); Sproat et al., Polynucleotides Res., 15:4837, (1987); and Nelson et al., Polynucleotides Res., 17:7187-7194, (1989), the contents of each of which are herein incorporated by reference in their entirety. Extensive guidance exists in the literature for derivatizing fluorophore and quencher molecules for covalent attachment via common reactive groups that may be added to a nucleotide. Many linking moieties and methods for attaching fluorophore moieties to nucleotides also exist, as described in Oligonucleotides and Analogues, supra; Guisti et al., supra; Agrawal et al, supra; and Sproat et al., supra The detectable label attached to the probe may be directly or indirectly detectable. In certain embodiments, the exact label may be selected based, at least in part, on the particular type of detection method used. Exemplary detection methods include radioactive detection, optical absorbance detection, e.g., UV-visible absorbance detection, optical emission detection, e.g., fluorescence; phosphorescence or chemiluminescence; Raman scattering. Preferred labels include optically-detectable labels, such as fluorescent labels. Examples of fluorescent labels include, but are not limited to, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; alexa; fluorescien; conjugated multi-dyes; Brilliant Yellow; coumarin and derivatives; coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5'5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N', N'tetramethyl-6-carboxyrhodamine (TAMRA); tetramethyl rhodamine; tetramethyl rhodamine isothiocyanate (TRITC); riboflavin; rosolic acid; terbium chelate derivatives; Atto dyes, Cy3; Cy5; Cy5.5; Cy7; IRD 700; IRD 800; La Jolta Blue; phthalo cyanine; and naphthalo cyanine. Labels other than fluorescent labels are contemplated by the invention, including other optically-detectable labels.

Detection of a bound probe may be measured using any of a variety of techniques dependent upon the label used, such as those known to one of skill in the art. Exemplary detection methods include radioactive detection, optical absorbance detection, e.g., UV-visible absorbance detection, optical emission detection, e.g., fluorescence or chemiluminescence. Devices capable of sensing fluorescence from a single molecule include scanning tunneling microscope (siM) and the atomic force microscope (AFM). Hybridization patterns may also be scanned using a CCD camera (e.g., Model TE/CCD512SF, Princeton Instruments, Trenton, N.J.) with suitable optics (Ploem, in Fluorescent and Luminescent Probes for Biological Activity Mason, T. G. Ed., Academic Press, Landon, pp. 1-11 (1993)), such as described in Yershov et al., Proc. Natl. Acad. Sci. 93:4913 (1996), or may be imaged by TV monitoring. For radioactive signals, a phosphorimager device can be used (Johnston et al., Electrophoresis, 13:566, 1990; Drmanac et al., Electrophoresis, 13:566, 1992; 1993). Other commercial suppliers of imaging instruments include General Scanning Inc., (Watertown, Mass. on the World Wide Web at genscan.com), Genix Technologies (Waterloo, Ontario, Canada; on the World Wide Web at confocal.com), and Applied Precision Inc.

In certain embodiments, the target nucleic acid or nucleic acid ligand or both are quantified using methods known in the art. A preferred method for quantitation is quantitative polymerase chain reaction (QPCR). As used herein, "QPCR" refers to a PCR reaction performed in such a way and under such controlled conditions that the results of the assay are quantitative, that is, the assay is capable of quantifying the amount or concentration of a nucleic acid ligand present in the test sample.

QPCR is a technique based on the polymerase chain reaction, and is used to amplify and simultaneously quantify a targeted nucleic acid molecule. QPCR allows for both detection and quantification (as absolute number of copies or relative amount when normalized to DNA input or additional normalizing genes) of a specific sequence in a DNA sample. The procedure follows the general principle of PCR, with the additional feature that the amplified DNA is quantified as it accumulates in the reaction in real time after each amplification cycle. QPCR is described, for example, in Kurnit et al. (U.S. Pat. No. 6,033,854), Wang et al. (U.S. Pat. Nos. 5,567, 583 and 5,348,853), Ma et al. (The Journal of American Science, 2(3), (2006)), Heid et al. (Genome Research 986-994, (1996)), Sambrook and Russell (Quantitative PCR, Cold Spring Harbor Protocols, (2006)), and Higuchi (U.S. Pat. Nos. 6,171,785 and 5,994,056). The contents of these are incorporated by reference herein in their entirety.

Two common methods of quantification are: (1) use of fluorescent dyes that intercalate with double-stranded DNA, and (2) modified DNA oligonucleotide probes that fluoresce when hybridized with a complementary DNA.

In the first method, a DNA-binding dye binds to all double-stranded (ds)DNA in PCR, resulting in fluorescence of the dye. An increase in DNA product during PCR therefore leads to an increase in fluorescence intensity and is measured at each cycle, thus allowing DNA concentrations to be quantified. The reaction is prepared similarly to a standard PCR reaction, with the addition of fluorescent (ds)DNA dye. The reaction is run in a thermocycler, and after each cycle, the levels of fluorescence are measured with a detector; the dye only fluoresces when bound to the (ds)DNA (i.e., the PCR product). With reference to a standard dilution, the (ds)DNA concentration in the PCR can be determined. Like other real-time PCR methods, the values obtained do not have absolute units associated with it. A comparison of a measured DNA/

RNA sample to a standard dilution gives a fraction or ratio of the sample relative to the standard, allowing relative comparisons between different tissues or experimental conditions. To ensure accuracy in the quantification, it is important to normalize expression of a target gene to a stably expressed gene. This allows for correction of possible differences in nucleic acid quantity or quality across samples.

The second method uses sequence-specific RNA or DNA-based probes to quantify only the DNA containing the probe sequence; therefore, use of the reporter probe significantly increases specificity, and allows for quantification even in the presence of some non-specific DNA amplification. This allows for multiplexing, i.e., assaying for several genes in the same reaction by using specific probes with differently colored labels, provided that all genes are amplified with similar efficiency.

This method is commonly carried out with a DNA-based probe with a fluorescent reporter (e.g. 6-carboxyfluorescein) at one end and a quencher (e.g., 6-carboxy-tetramethylrhodamine) of fluorescence at the opposite end of the probe. The close proximity of the reporter to the quencher prevents detection of its fluorescence. Breakdown of the probe by the 5' to 3' exonuclease activity of a polymerase (e.g., Taq polymerase) breaks the reporter-quencher proximity and thus allows unquenched emission of fluorescence, which can be detected. An increase in the product targeted by the reporter probe at each PCR cycle results in a proportional increase in fluorescence due to breakdown of the probe and release of the reporter. The reaction is prepared similarly to a standard PCR reaction, and the reporter probe is added. As the reaction commences, during the annealing stage of the PCR, both probe and primers anneal to the DNA target. Polymerization of a new DNA strand is initiated from the primers, and once the polymerase reaches the probe, its 5'-3'-exonuclease degrades the probe, physically separating the fluorescent reporter from the quencher, resulting in an increase in fluorescence. Fluorescence is detected and measured in a real-time PCR thermocycler, and geometric increase of fluorescence corresponding to exponential increase of the product is used to determine the threshold cycle in each reaction.

In certain embodiments, the QPCR reaction uses fluorescent Taqman™ methodology and an instrument capable of measuring fluorescence in real time (e.g., ABI Prism 7700 Sequence Detector; see also PE Biosystems, Foster City, Calif.; see also Gelfand et al., (U.S. Pat. No. 5,210,015), the contents of which is hereby incorporated by reference in its entirety). The Taqman™ reaction uses a hybridization probe labeled with two different fluorescent dyes. One dye is a reporter dye (6-carboxyfluorescein), the other is a quenching dye (6-carboxy-tetramethylrhodamine). When the probe is intact, fluorescent energy transfer occurs and the reporter dye fluorescent emission is absorbed by the quenching dye. During the extension phase of the PCR cycle, the fluorescent hybridization probe is cleaved by the 5'-3' nucleolytic activity of the DNA polymerase. On cleavage of the probe, the reporter dye emission is no longer transferred efficiently to the quenching dye, resulting in an increase of the reporter dye fluorescent emission spectra.

The nucleic acid ligand of the present invention is quantified by performing QPCR and determining, either directly or indirectly, the amount or concentration of nucleic acid ligand that had bound to its probe in the test sample. The amount or concentration of the bound probe in the test sample is generally directly proportional to the amount or concentration of the nucleic acid ligand quantified by using QPCR. See for example Schneider et al., U.S. Patent Application Publication Number 2009/0042206, Dodge et al., U.S. Pat. No. 6,927,024, Gold et al., U.S. Pat. Nos. 6,569,620, 6,716,580, and 7,629,151, Cheronis et al., U.S. Pat. No. 7,074,586, and Ahn et al., U.S. Pat. No. 7,642,056, the contents of each of which are herein incorporated by reference in their entirety.

Detecting the presence of the aptamer in the analyzed sample directly correlates to the presence of the target protein in that sample. In some embodiments of the invention, the amount of aptamer present in the sample correlates to the signal intensity following the conduction of the PCR-based methods. The signal intensity of PCR depends upon the number of PCR cycles performed and/or the starting concentration of the aptamer. Since the sequence of the target protein is known to generate the aptamer, detection of that specific aptamer correlates to the presence of the target protein. Similarly, detection of the amplified target nucleic acid indicates the presence of the target nucleic acid in the sample analyzed.

In one embodiment of the invention, during amplification of the aptamer or target nucleic acid using standard PCR methods, one method for detection and quantification of amplified aptamer or target nucleic acid results from the presence of a fluorogenic probe. In one embodiment of the invention, the probe, which is specific for the aptamer, has a 6-carboxyfluorescein (FAM) moiety covalently bound to the 5'-end and a 6-carboxytetramethylrhodamine (TAMRA) or other fluorescent-quenching dye (easily prepared using standard automated DNA synthesis) present on the 3'-end, along with a 3'-phosphate to prevent elongation. The probe is added with 5'-nuclease to the PCR assays, such that 5'-nuclease cleavage of the probe-aptamer duplex results in release of the 5'-bound FAM moiety from the oligonucleotide probe. As amplification continues and more aptamer is replicated by the PCR or RT-PCR enzymes, more FAM is released per cycle and so intensity of fluorescence signal per cycle increases. The relative increase in FAM emission is monitored during PCR or RT-PCR amplification using an analytical thermal cycler, or a combined thermal cycler/laser/detector/software system such as an ABI 7700 Sequence Detector (Applied Biosystems, Foster City, Calif.). The ABI instrument has the advantage of allowing analysis and display of quantification in less than 60 s upon termination of the amplification reactions. Both detection systems employ an internal control or standard wherein a second aptamer sequence utilizing the same primers for amplification but having a different sequence and thus different probe, is amplified, monitored and quantitated simultaneously as that for the desired target molecule. See for example, "A Novel Method for Real Time Quantitative RT-PCR," Gibson, U. et. al., 1996, Genome Res. 6:995-1001; Piatak, M. et. al., 1993, BioTechniques 14:70-81; "Comparison of the BI 7700 System (TaqMan) and Competitive PCR for Quantification of IS6110 DNA in Sputum During Treatment of Tuberculosis," Desjardin, L.e. et. al., 1998, J. Clin. Microbiol. 36(7):1964-1968), the contents of which are incorporated by reference, herein in their entirety.

In another method for detection and quantification of aptamer during amplification, the primers used for amplification contain molecular energy transfer (MET) moieties, specifically fluorescent resonance energy transfer (FRET) moieties, whereby the primers contain both a donor and an acceptor molecule. The FRET pair typically contains a fluorophore donor moiety such as 5-carboxyfluorescein (FAM) or 6-carboxy-4,5-dichloro-2,7-dimethoxyfluorescein (JOE), with an emission maximum of 525 or 546 nm, respectively, paired with an acceptor moiety such as N'N'N'N'-tetramethyl-6-carboxyrhodamine (TAMRA), 6-carboxy-X-rhodamine (ROX) or 6-carboxyrhodamine (R6G), all of which have excitation maximum of 514 nm. The primer may be a hairpin such that the 5'-end of the primer contains the FRET donor, and the 3'-end (based-paired to the 5'-end to form the stem region of the hairpin) contains the FRET acceptor, or quencher. The two moieties in the FRET pair are separated by approximately 15-25 nucleotides in length when the hairpin primer is linearized. While the primer is in the hairpin conformation, no fluorescence is detected. Thus, fluorescence by the donor is only detected when the primer is in a linearized conformation, i.e. when it is incorporated into a double-stranded amplification product. Such a method allows direct quantification of the amount of aptamer bound to target molecule in the sample mixture, and this quantity is then used to determine the amount of target molecule originally present in the sample. See for example, Nazarenko, I. A. et al., U.S. Pat. No. 5,866,336, the contents of which is incorporated by reference in its entirety.

In another embodiment of the invention, the QPCR reaction using TaqMan™ methodology selects a TaqMan™ probe based upon the sequence of the aptamer to be quantified and generally includes a 5'-end fluor, such as 6-carboxyfluorescein, for example, and a 3'-end quencher, such as, for example, a 6-carboxytetramethylfluorescein, to generate signal as the aptamer sequence is amplified using PCR. As the polymerase copies the aptamer sequence, the exonuclease activity frees the fluor from the probe, which is annealed downstream from the PCR primers, thereby generating signal. The signal increases as replicative product is produced. The amount of PCR product depends upon both the number of replicative cycles performed as well as the starting concentration of the aptamer. In another embodiment, the amount or concentration of an aptamer affinity complex (or aptamer covalent complex) is determined using an intercalating fluorescent dye during the replicative process. The intercalating dye, such as, for example, SYBR™ green, generates a large fluorescent signal in the presence of double-stranded DNA as compared to the fluorescent signal generated in the presence of single-stranded DNA. As the double-stranded DNA product is formed during PCR, the signal produced by the dye increases. The magnitude of the signal produced is dependent upon both the number of PCR cycles and the starting concentration of the aptamer.

Nucleic acids and proteins may be obtained by methods known in the art. Generally, nucleic acids can be extracted from a biological sample by a variety of techniques such as those described by Maniatis, et al., Molecular Cloning: A Laboratory Manual, Cold Spring Harbor, N.Y., pp. 280-281, (1982), the contents of which is incorporated by reference herein in its entirety. Generally, proteins can be extracted from a biological sample by a variety of techniques such as 2-D electrophoresis, isoelectric focusing, and SDS Slab Gel Electrophoresis. See for example O'Farrell, J. Biol. Chem., 250: 4007-4021 (1975), Sambrook, J. et al., Molecular Cloning: a Laboratory Manual, 2nd Edition, Cold Spring Harbor Laboratory Press, Cold Spring Harbor, N.Y. (1989), Anderson et al., U.S. Pat. No. 6,391,650, Shepard, U.S. Pat. No. 7,229,789, and Han et al., U.S. Pat. No. 7,488,579 the contents of each of which is hereby incorporated by reference in its entirety.

In other embodiments, antibodies with a unique oligonucleotide tag are added to the sample to bind a target protein and detection of the oligonucleotide tag results in detection of the protein. The target protein is exposed to an antibody that is coupled to an oligonucleotide tag of a known sequence. The antibody specifically binds the protein, and then PCR is used to amplify the oligonucleotide coupled to the antibody. The identity of the target protein is determined based upon the sequence of the oligonucleotide attached to the antibody and the presence of the oligonucleotide in the sample. In this embodiment of the invention, different antibodies specific for the target protein are used. Each antibody is coupled to a unique oligonucleotide tag of known sequence. Therefore, more than one target protein can be detected in a sample by identifying the unique oligonucleotide tag attached to the antibody. See for example Kahvejian, U.S. Patent Application Publication Number 2007/0020650, hereby incorporated by reference.

In other embodiments of the invention, antibodies with a unique nucleotide tag are added to the sample to bind the target nucleic acid. As described above, different antibodies specific for the target nucleic acid are used, therefore, more than one target nucleic acid can be detected in a sample by identifying the unique oligonucleotide tag attached. Detection of the nucleotide tag may be done by methods known in the art, such as PCR, QPCR, fluorescent labeling, radiolabeling, biotinylation, Sanger sequencing, sequencing by synthesis, or Single Molecule Real Time Sequencing methods. For description of single molecule sequencing methods see for example, Lapidus, U.S. Pat. No. 7,666,593, Quake et al., U.S. Pat. No. 7,501,245, and Lapidus et al., U.S. Pat. Nos. 7,169,560 and 7,491,498, the contents of each of which are herein incorporated by reference.

Antibodies for use in the present invention can be generated by methods well known in the art. See, for example, E. Harlow and D. Lane, Antibodies, a Laboratory Model, Cold Spring Harbor Laboratory Press, Cold Spring Harbor, N.Y., (1988), the contents of which are hereby incorporated by reference in their entirety. In addition, a wide variety of antibodies are available commercially.

The antibody can be obtained from a variety of sources, such as those known to one of skill in the art, including but not limited to polyclonal antibody, monoclonal antibody, monospecific antibody, recombinantly expressed antibody, humanized antibody, plantibodies, and the like; and can be obtained from a variety of animal species, including rabbit, mouse, goat, rat, human, horse, bovine, guinea pig, chicken, sheep, donkey, human, and the like. A wide variety of antibodies are commercially available and a custom-made antibody can be obtained from a number of contract labs. Detailed descriptions of antibodies, including relevant protocols, can be found in, among other places, Current Protocols in Immunology, Coligan et al., eds., John Wiley & Sons (1999, including updates through August 2003); The Electronic Notebook; Basic Methods in Antibody Production and Characterization, G. Howard and D. Bethel, eds., CRC Press (2000); J. Coding, Monoclonal Antibodies: Principles and Practice, 3d Ed., Academic Press (1996); E. Harlow and D. Lane, Using Antibodies, Cold Spring Harbor Lab Press (1999); P. Shepherd and C. Dean, Monoclonal Antibodies: A Practical Approach, Oxford University Press (2000); A. Johnstone and M. Turner, Immunochemistry 1 and 2, Oxford University Press (1997); C. Borrebaeck, Antibody Engineering, 2d ed., Oxford university Press (1995); A. Johnstone and R. Thorpe, Immunochemistry in Practice, Blackwell Science, Ltd. (1996); H. Zola, Monoclonal Antibodies: Preparation and Use of Monoclonal Antibodies and Engineered Antibody Derivatives (Basics: From Background to Bench), Springer Verlag (2000); and S. Hockfield et al., Selected Methods for Antibody and Nucleic Acid Probes, Cold Spring Harbor Lab Press (1993).

In certain embodiments, the target nucleic acid or nucleic acid ligand or both are detected using sequencing. In those embodiments, the aptamer/protein complex may be dissociated, releasing the aptamer for the sequencing reaction. Sequencing-by-synthesis is a common technique used in next generation procedures and works well with the instant invention. However, other sequencing methods can be used, including sequence-by-ligation, sequencing-by-hybridization, gel-based techniques and others. In general, sequencing involves hybridizing a primer to a template to form a template/primer duplex, contacting the duplex with a polymerase in the presence of a detectably-labeled nucleotides under conditions that permit the polymerase to add nucleotides to the primer in a template-dependent manner. Signal from the detectable label is then used to identify the incorporated base and the steps are sequentially repeated in order to determine the linear order of nucleotides in the template. Exemplary detectable labels include radiolabels, florescent labels, enzymatic labels, etc. In particular embodiments, the detectable label may be an optically detectable label, such as a fluorescent label. Exemplary fluorescent labels include cyanine, rhodamine, fluorescien, coumarin, BODIPY, alexa, or conjugated multi-dyes. Numerous techniques are known for detecting sequences and some are exemplified below. However, the exact means for detecting and compiling sequence data does not affect the function of the invention described herein.

A sequencing technique that can be used in the methods of the provided invention includes, for example, Helicos True Single Molecule Sequencing (tSMS) (Harris T. D. et al. (2008) Science 320:106-109). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. The templates can be at a density of about 100 million templates/cm$^2$. The flow cell is then loaded into an instrument, e.g., HeliScope™ sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are detected by imaging the flow cell surface. After imaging, a cleavage step removes the fluorescent label, and the process is repeated with other fluorescently labeled nucleotides until the desired read length is achieved. Sequence information is collected with each nucleotide addition step. Further description of tSMS is shown for example in Lapidus et al. (U.S. Pat. No. 7,169,560), Lapidus et al. (U.S. patent application number 2009/0191565), Quake et al. (U.S. Pat. No. 6,818,395), Harris (U.S. Pat. No. 7,282,337), Quake et al. (U.S. patent application number 2002/0164629), and Braslaysky, et al., PNAS (USA), 100: 3960-3964 (2003), the contents of each of these references is incorporated by reference herein in its entirety.

Another example of a DNA sequencing technique that can be used in the methods of the provided invention is 454 sequencing (Roche) (Margulies, M et al. 2005, Nature, 437, 376-380). 454 sequencing involves two steps. In the first step, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is detected and analyzed.

Another example of a DNA sequencing technique that can be used in the methods of the provided invention is SOLiD technology (Applied Biosystems). In SOLiD sequencing, genomic DNA is sheared into fragments, and adaptors are attached to the 5' and 39' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

Another example of a DNA sequencing technique that can be used in the methods of the provided invention is Ion Torrent sequencing (U.S. patent application numbers 2009/0026082, 2009/0127589, 2010/0035252, 2010/0137143, 2010/0188073, 2010/0197507, 2010/0282617, 2010/0300559), 2010/0300895, 2010/0301398, and 2010/0304982), the content of each of which is incorporated by reference herein in its entirety. In Ion Torrent sequencing, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to a surface and is attached at a resolution such that the fragments are individually resolvable. Addition of one or more nucleotides releases a proton ($H^+$), which signal detected and recorded in a sequencing instrument. The signal strength is proportional to the number of nucleotides incorporated.

Another example of a sequencing technology that can be used in the methods of the provided invention is Illumina sequencing. Illumina sequencing is based on the amplification of DNA on a solid surface using fold-back PCR and anchored primers. Genomic DNA is fragmented, and adapters are added to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated.

Another example of a sequencing technology that can be used in the methods of the provided invention includes the single molecule, real-time (SMRT) technology of Pacific Biosciences. In SMRT, each of the four DNA bases is attached to one of four different fluorescent dyes. These dyes are phospholinked. A single DNA polymerase is immobilized with a single molecule of template single stranded DNA at the bottom of a zero-mode waveguide (ZMW). A ZMW is a confinement structure which enables observation of incorporation of a single nucleotide by DNA polymerase against the background of fluorescent nucleotides that rapidly diffuse in an out of the ZMW (in microseconds). It takes several milliseconds to incorporate a nucleotide into a growing strand. During this time, the fluorescent label is excited and produces a fluorescent signal, and the fluorescent tag is cleaved off. Detection of the corresponding fluorescence of the dye indicates which base was incorporated. The process is repeated.

Another example of a sequencing technique that can be used in the methods of the provided invention is nanopore sequencing (Soni G V and Meller A. (2007) Clin Chem 53: 1996-2001). A nanopore is a small hole, of the order of 1 nanometer in diameter. Immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence.

Another example of a sequencing technique that can be used in the methods of the provided invention involves using a chemical-sensitive field effect transistor (chemFET) array to sequence DNA (for example, as described in US Patent Application Publication No. 20090026082). In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be detected by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

Another example of a sequencing technique that can be used in the methods of the provided invention involves using a electron microscope (Moudrianakis E. N. and Beer M. Proc Natl Acad Sci USA. 1965 March; 53:564-71). In one example of the technique, individual DNA molecules are labeled using metallic labels that are distinguishable using an electron microscope. These molecules are then stretched on a flat surface and imaged using an electron microscope to measure sequences.

Sequences can be read that originate from a single molecule or that originate from amplifications from a single molecule Millions of independent amplifications of single molecules can be performed in parallel either on a solid surface or in tiny compartments in water/oil emulsion. The DNA sample to be sequenced can be diluted and/or dispersed sufficiently to obtain one molecule in each compartment. This dilution can be followed by DNA amplification to generate copies of the original DNA sequences and creating "clusters" of molecules all having the same sequence. These clusters can then be sequenced. Many millions of reads can be generated in one run. Sequence can be generated starting at the 5' end of a given strand of an amplified sequence and/or sequence can be generated from starting from the 5' end of the complementary sequence. In a preferred embodiment, sequence from strands is generated, i.e. paired end reads (see for example, Harris, U.S. Pat. No. 7,767,400).

Nucleotides useful in the invention include any nucleotide or nucleotide analog, whether naturally-occurring or synthetic. For example, preferred nucleotides include phosphate esters of deoxyadenosine, deoxycytidine, deoxyguanosine, deoxythymidine, adenosine, cytidine, guanosine, and uridine. Other nucleotides useful in the invention comprise an adenine, cytosine, guanine, thymine base, a xanthine or hypoxanthine; 5-bromouracil, 2-aminopurine, deoxyinosine, or methylated cytosine, such as 5-methylcytosine, and N4-methoxydeoxycytosine. Also included are bases of polynucleotide mimetics, such as methylated nucleic acids, e.g., 2'-O-methRNA, peptide nucleic acids, modified peptide nucleic acids, locked nucleic acids and any other structural moiety that can act substantially like a nucleotide or base, for example, by exhibiting base-complementarity with one or more bases that occur in DNA or RNA and/or being capable of base-complementary incorporation, and includes chain-terminating analogs. A nucleotide corresponds to a specific nucleotide species if they share base-complementarity with respect to at least one base.

Nucleotides for nucleic acid sequencing according to the invention preferably include a detectable label that is directly or indirectly detectable. Preferred labels include optically-detectable labels, such as fluorescent labels. Examples of fluorescent labels include, but are not limited to, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5'5''-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N', N'tetramethyl-6-carboxyrhodamine (TAMRA); tetramethyl rhodamine; tetramethyl rhodamine isothiocyanate (TRITC); riboflavin; rosolic acid; terbium chelate derivatives; Cy3; Cy5; Cy5.5; Cy7; IRD 700; IRD 800; La Jolta Blue; phthalo cyanine; and naphthalo cyanine. Preferred fluorescent labels are cyanine-3 and cyanine-5. Labels other than fluorescent labels are contemplated by the invention, including other optically-detectable labels.

Nucleic acid polymerases generally useful in the invention include DNA polymerases, RNA polymerases, reverse transcriptases, and mutant or altered forms of any of the foregoing. DNA polymerases and their properties are described in detail in, among other places, DNA Replication 2nd edition, Kornberg and Baker, W. H. Freeman, New York, N.Y. (1991). Known conventional DNA polymerases useful in the invention include, but are not limited to, *Pyrococcus furiosus* (Pfu) DNA polymerase (Lundberg et al., 1991, Gene, 108: 1, Stratagene), *Pyrococcus woesei* (Pwo) DNA polymerase (Hinnisdaels et al., 1996, Biotechniques, 20:186-8, Boehringer Mannheim), *Thermus thermophilus* (Tth) DNA polymerase (Myers and Gelfand 1991, Biochemistry 30:7661), *Bacillus stearothermophilus* DNA polymerase (Stenesh and McGowan, 1977, Biochim Biophys Acta 475:32), *Thermococcus litoralis* (Tli) DNA polymerase (also referred to as Vent™ DNA polymerase, Cariello et al., 1991, Polynucleotides Res, 19: 4193, New England Biolabs), 9.degree.Nm™ DNA polymerase (New England Biolabs), Stoffel fragment, ThermoSequenase® (Amersham Pharmacia Biotech UK), Therminator™ (New England Biolabs), *Thermotoga maritima* (Tma) DNA polymerase (Diaz and Sabino, 1998 Braz J. Med. Res, 31:1239), *Thermus aquaticus* (Taq) DNA polymerase (Chien et al., 1976, J. Bacteoriol, 127: 1550), DNA polymerase, *Pyrococcus kodakaraensis* KOD DNA polymerase (Takagi et al., 1997, Appl. Environ. Microbiol. 63:4504), JDF-3 DNA polymerase (from *thermococcus* sp. JDF-3, Patent application WO 0132887), *Pyrococcus* GB-D (PGB-D) DNA polymerase (also referred as Deep Vent™ DNA polymerase, Juncosa-Ginesta et al., 1994, Biotechniques, 16:820, New England Biolabs), UlTma DNA polymerase (from thermophile *Thermotoga maritima*; Diaz and Sabino, 1998 Braz J. Med. Res, 31:1239; PE Applied Biosystems), Tgo DNA polymerase (from *thermococcus gorgonarius*, Roche Molecular Biochemicals), *E. coli* DNA polymerase I (Lecomte and Doubleday, 1983, Polynucleotides Res. 11:7505), T7 DNA polymerase (Nordstrom et al., 1981, J. Biol. Chem. 256:3112), and archaeal DP1I/DP2 DNA polymerase II (Cann et al, 1998, Proc. Natl. Acad. Sci. USA 95:14250).

Both mesophilic polymerases and thermophilic polymerases are contemplated. Thermophilic DNA polymerases include, but are not limited to, ThermoSequenase®, 9.degree.Nm™, Therminator™, Taq, Tne, Tma, Pfu, Tfl, Tth, Tli, Stoffel fragment, Vent™ and Deep Vent™ DNA polymerase, KOD DNA polymerase, Tgo, JDF-3, and mutants, variants and derivatives thereof. A highly-preferred form of any polymerase is a 3' exonuclease-deficient mutant.

Reverse transcriptases useful in the invention include, but are not limited to, reverse transcriptases from HIV, HTLV-1, HTLV-II, FeLV, FIV, SIV, AMV, MMTV, MoMuLV and other retroviruses (see Levin, Cell 88:5-8 (1997); Verma, Biochim Biophys Acta. 473:1-38 (1977); Wu et al., CRC Crit. Rev Biochem. 3:289-347 (1975)).

In a preferred embodiment, nucleic acid template molecules are attached to a substrate (also referred to herein as a surface) and subjected to analysis by single molecule sequencing as described herein. Nucleic acid template molecules are attached to the surface such that the template/primer duplexes are individually optically resolvable. Substrates for use in the invention can be two- or three-dimensional and can comprise a planar surface (e.g., a glass slide) or can be shaped. A substrate can include glass (e.g., controlled pore glass (CPG)), quartz, plastic (such as polystyrene (low cross-linked and high cross-linked polystyrene), polycarbonate, polypropylene and poly(methymethacrylate)), acrylic copolymer, polyamide, silicon, metal (e.g., alkanethiolate-derivatized gold), cellulose, nylon, latex, dextran, gel matrix (e.g., silica gel), polyacrolein, or composites.

Suitable three-dimensional substrates include, for example, spheres, microparticles, beads, membranes, slides, plates, micromachined chips, tubes (e.g., capillary tubes), microwells, microfluidic devices, channels, filters, or any other structure suitable for anchoring a nucleic acid. Substrates can include planar arrays or matrices capable of having regions that include populations of template nucleic acids or primers. Examples include nucleoside-derivatized CPG and polystyrene slides; derivatized magnetic slides; polystyrene grafted with polyethylene glycol, and the like.

Substrates are preferably coated to allow optimum optical processing and nucleic acid attachment. Substrates for use in the invention can also be treated to reduce background. Exemplary coatings include epoxides, and derivatized epoxides (e.g., with a binding molecule, such as an oligonucleotide or streptavidin).

Various methods can be used to anchor or immobilize the nucleic acid molecule to the surface of the substrate. The immobilization can be achieved through direct or indirect bonding to the surface. The bonding can be by covalent linkage. See, Joos et al., Analytical Biochemistry 247:96-101, 1997; Oroskar et al., Clin. Chem. 42:1547-1555, 1996; and Khandjian, Mol. Bio. Rep. 11:107-115, 1986. A preferred attachment is direct amine bonding of a terminal nucleotide of the template or the 5' end of the primer to an epoxide integrated on the surface. The bonding also can be through non-covalent linkage. For example, biotin-streptavidin (Taylor et al., J. Phys. D. Appl. Phys. 24:1443, 1991) and digoxigenin with anti-digoxigenin (Smith et al., Science 253:1122, 1992) are common tools for anchoring nucleic acids to surfaces and parallels. Alternatively, the attachment can be achieved by anchoring a hydrophobic chain into a lipid monolayer or bilayer. Other methods for known in the art for attaching nucleic acid molecules to substrates also can be used.

Any detection method can be used that is suitable for the type of label employed. Thus, exemplary detection methods include radioactive detection, optical absorbance detection, e.g., UV-visible absorbance detection, optical emission detection, e.g., fluorescence or chemiluminescence. For example, extended primers can be detected on a substrate by scanning all or portions of each substrate simultaneously or serially, depending on the scanning method used. For fluorescence labeling, selected regions on a substrate may be serially scanned one-by-one or row-by-row using a fluorescence microscope apparatus, such as described in Fodor (U.S. Pat. No. 5,445,934) and Mathies et al. (U.S. Pat. No. 5,091, 652). Devices capable of sensing fluorescence from a single molecule include scanning tunneling microscope (siM) and the atomic force microscope (AFM). Hybridization patterns may also be scanned using a CCD camera (e.g., Model TE/CCD512SF, Princeton Instruments, Trenton, N.J.) with suitable optics (Ploem, in Fluorescent and Luminescent Probes for Biological Activity Mason, T. G. Ed., Academic Press, Landon, pp. 1-11 (1993), such as described in Yershov et al., Proc. Natl. Acad. Sci. 93:4913 (1996), or may be imaged by TV monitoring. For radioactive signals, a phosphorimager device can be used (Johnston et al., Electrophoresis, 13:566, 1990; Drmanac et al., Electrophoresis, 13:566, 1992; 1993). Other commercial suppliers of imaging instruments include General Scanning Inc., (Watertown, Mass. on the World Wide Web at genscan.com), Genix Technologies (Waterloo, Ontario, Canada; on the World Wide Web at confocal.com), and Applied Precision Inc. Such detection methods are particularly useful to achieve simultaneous scanning of multiple attached template nucleic acids.

A number of approaches can be used to detect incorporation of fluorescently-labeled nucleotides into a single nucleic acid molecule. Optical setups include near-field scanning microscopy, far-field confocal microscopy, wide-field epi-illumination, light scattering, dark field microscopy, photoconversion, single and/or multiphoton excitation, spectral wavelength discrimination, fluorophor identification, evanescent wave illumination, and total internal reflection fluorescence (TIRF) microscopy. In general, certain methods involve detection of laser-activated fluorescence using a microscope equipped with a camera. Suitable photon detection systems include, but are not limited to, photodiodes and intensified CCD cameras. For example, an intensified charge couple device (ICCD) camera can be used. The use of an ICCD camera to image individual fluorescent dye molecules in a fluid near a surface provides numerous advantages. For example, with an ICCD optical setup, it is possible to acquire a sequence of images (movies) of fluorophores.

Some embodiments of the present invention use TIRF microscopy for imaging. TIRF microscopy uses totally internally reflected excitation light and is well known in the art. See, e.g., the World Wide Web at nikon-instruments.jp/eng/page/products/tirf.aspx. In certain embodiments, detection is carried out using evanescent wave illumination and total internal reflection fluorescence microscopy. An evanescent light field can be set up at the surface, for example, to image fluorescently-labeled nucleic acid molecules. When a laser beam is totally reflected at the interface between a liquid and a solid substrate (e.g., a glass), the excitation light beam penetrates only a short distance into the liquid. The optical field does not end abruptly at the reflective interface, but its intensity falls off exponentially with distance. This surface electromagnetic field, called the "evanescent wave", can selectively excite fluorescent molecules in the liquid near the interface. The thin evanescent optical field at the interface provides low background and facilitates the detection of single molecules with high signal-to-noise ratio at visible wavelengths.

The evanescent field also can image fluorescently-labeled nucleotides upon their incorporation into the attached template/primer complex in the presence of a polymerase. Total internal reflectance fluorescence microscopy is then used to visualize the attached template/primer duplex and/or the incorporated nucleotides with single molecule resolution.

Some embodiments of the invention use non-optical detection methods such as, for example, detection using nanopores (e.g., protein or solid state) through which molecules are individually passed so as to allow identification of the molecules by noting characteristics or changes in various properties or effects such as capacitance or blockage current flow (see, for example, Stoddart et al, Proc. Nat. Acad. Sci., 106:7702, 2009; Purnell and Schmidt, ACS Nano, 3:2533, 2009; Branton et al, Nature Biotechnology, 26:1146, 2008; Polonsky et al, U.S. Application 2008/0187915; Mitchell & Howorka, Angew. Chem. Int. Ed. 47:5565, 2008; Borsenberger et al, J. Am. Chem. Soc., 131, 7530, 2009) ; or other suitable non-optical detection methods.

Alignment and/or compilation of sequence results obtained from the image stacks produced as generally described above utilizes look-up tables that take into account possible sequences changes (due, e.g., to errors, mutations, etc.). Essentially, sequencing results obtained as described herein are compared to a look-up type table that contains all possible reference sequences plus 1 or 2 base errors.

In some embodiments, a plurality of nucleic acid molecules being sequenced are bound to a solid support. To immobilize the nucleic acid on a solid support, a capture sequence/universal priming site can be added at the 3' and/or 5' end of the template. The nucleic acids may be bound to the solid support by hybridizing the capture sequence to a complementary sequence covalently attached to the solid support. The capture sequence (also referred to as a universal capture sequence) is a nucleic acid sequence complimentary to a sequence attached to a solid support that may dually serve as a universal primer. In some embodiments, the capture sequence is $polyN_n$, wherein N is U, A, T, G, or C, e g., 20-70, 40-60, e.g., about 50. For example, the capture sequence could be $polyT_{40-50}$ or its complement. As an alternative to a capture sequence, a member of a coupling pair (such as, e.g., antibody/antigen, receptor/ligand, or the avidin-biotin pair as described in, e.g., U.S. Patent Application No. 2006/0252077) may be linked to each fragment to be captured on a surface coated with a respective second member of that coupling pair.

In some embodiments, a barcode sequence is attached to the nucleic acid, the aptamer, or both. See for example, Steinman et al. (PCT internal application number PCT/US09/64001), the content of which is incorporated by reference herein in its entirety.

Methods of the invention can be used to detect biomarkers, such as those described above. Examples of preferred biomarkers include FGFR3, K-ras, K-ras2, APC, DCC, TP53, PRC1, NUSAPI1, CAPZ, PFKP, EVER1, FLT1, ESPL1, AKAP2, CDC45L, RAMP, SYNGR2, NDRG1, ZNF533, and hypermethylated nucleic acid.

In certain embodiments, the disease is a cancer. Biomarkers that are associated with cancer are known in the art. Methods of the invention can look for nucleic acid mutations or quantify levels of cancer associated biomarkers to thereby diagnose a cancer. Biomarkers associated with development of breast cancer are shown in Erlander et al. (U.S. Pat. No. 7,504,214), Dai et al. (U.S. Pat. No. 7,514,209 and 7,171,311), Baker et al. (U.S. Pat. Nos. 7,056,674 and 7,081,340), Erlander et al. (US 2009/0092973). The contents of the patent application and each of these patents are incorporated by reference herein in their entirety. Biomarkers associated with development of cervical cancer are shown in Patel (U.S. Pat. No. 7,300,765), Pardee et al. (U.S. Pat. No. 7,153,700), Kim (U.S. Pat. No. 6,905,844), Roberts et al. (U.S. Pat. No. 6,316,208), Schlegel (US 2008/0113340), Kwok et al. (US 2008/0044828), Fisher et al. (US 2005/0260566), Sastry et al. (US 2005/0048467), Lai (US 2008/0311570) and Van Der Zee et al. (US 2009/0023137). Biomarkers associated with development of vaginal cancer are shown in Giordano (U.S. Pat. No. 5,840,506), Kruk (US 2008/0009005), Hellman et al. (Br J Cancer. 100(8):1303-1314, 2009). Biomarkers associated with development of brain cancers (e.g., glioma, cerebellum, medulloblastoma, astrocytoma, ependymoma, glioblastoma) are shown in D'Andrea (US 2009/0081237), Murphy et al. (US 2006/0269558), Gibson et al. (US 2006/0281089), and Zetter et al. (US 2006/0160762). Biomarkers associated with development of renal cancer are shown in Patel (U.S. Pat. No. 7,300,765), Soyupak et al. (U.S. Pat. No. 7,482,129), Sahin et al. (U.S. Pat. No. 7,527,933), Price et al. (U.S. Pat. No. 7,229,770), Raitano (U.S. Pat. No. 7,507,541), and Becker et al. (US 2007/0292869). Biomarkers associated with development of hepatic cancers (e.g., hepatocellular carcinoma) are shown in Home et al. (U.S. Pat. No. 6,974,667), Yuan et al. (U.S. Pat. No. 6,897,018), Hanausek-Walaszek et al. (U.S. Pat. No. 5,310,653), and Liew et al. (US 2005/0152908). Biomarkers associated with development of gastric, gastrointestinal, and/or esophageal cancers are shown in Chang et al. (U.S. Pat. No. 7,507,532), Bae et al. (U.S. Pat. No. 7,368,255), Muramatsu et al. (U.S. Pat. No. 7,090,983), Sahin et al. (U.S. Pat. No. 7,527,933), Chow et al. (US 2008/0138806), Waldman et al. (US 2005/0100895), Goldenring (US 2008/0057514), An et al. (US 2007/0259368), Guilford et al. (US 2007/0184439), Wirtz et al. (US 2004/0018525), Filella et al. (Acta Oncol. 33(7):747-751, 1994), Waldman et al. (U.S. Pat. No. 6,767,704), and Lipkin et al. (Cancer Research, 48:235-245, 1988). Biomarkers associated with development of ovarian cancer are shown in Podust et al. (U.S. Pat. No. 7,510,842), Wang (U.S. Pat. No. 7,348,142), O'Brien et al. (U.S. Pat. Nos. 7,291,462, 6,942,978, 6,316,213, 6,294,344, and 6,268,165), Ganetta (U.S. Pat. No. 7,078,180), Malinowski et al. (US 2009/0087849), Beyer et al. (US 2009/0081685), Fischer et al. (US 2009/0075307), Mansfield et al. (US 2009/0004687), Livingston et al. (US 2008/0286199), Farias-Eisner et al. (US 2008/0038754), Ahmed et al. (US 2007/0053896), Giordano (U.S. Pat. No. 5,840,506), and Tchagang et al. (Mol Cancer Ther, 7:27-37, 2008). Biomarkers associated with development of head-and-neck and thyroid cancers are shown in Sidransky et al. (U.S. Pat. No. 7,378,233), Skolnick et al. (U.S. Pat. No. 5,989,815), Budiman et al. (US 2009/0075265), Hasina et al. (Cancer Research, 63:555-559, 2003), Kebebew et al. (US 2008/0280302), and Ralhan (Mol Cell Proteomics, 7(6):1162-1173, 2008). The contents of each of the articles, patents, and patent applications are incorporated by reference herein in their entirety. Biomarkers associated with development of colorectal cancers are shown in Raitano et al. (U.S. Pat. No. 7,507,541), Reinhard et al. (U.S. Pat. No. 7,501,244), Waldman et al. (U.S. Pat. No. 7,479,376); Schleyer et al. (U.S. Pat. No. 7,198,899); Reed (U.S. Pat. No. 7,163,801), Robbins et al. (U.S. Pat. No. 7,022,472), Mack et al. (U.S. Pat. No. 6,682,890), Tabiti et al. (U.S. Pat. No. 5,888,746), Budiman et al. (US 2009/0098542), Karl (US 2009/0075311), Arjol et al. (US 2008/0286801), Lee et al. (US 2008/0206756), Mori et al. (US 2008/0081333), Wang et al. (US 2008/0058432), Belacel et al. (US 2008/0050723), Stedronsky et al. (US 2008/0020940), An et al. (US 2006/0234254), Eveleigh et al. (US 2004/0146921), and Yeatman et al. (US 2006/0195269). Biomarkers associated with development of prostate cancer are shown in Sidransky (U.S. Pat. No. 7,524,633), Platica (U.S. Pat. No. 7,510,707), Salceda et al. (U.S. Pat. Nos. 7,432,064 and 7,364,862), Siegler et al. (U.S. Pat. No. 7,361,474), Wang (U.S. Pat. No. 7,348,142), Ali et al. (U.S. Pat. No. 7,326,529), Price et al. (U.S. Pat. No. 7,229,770), O'Brien et al. (U.S. Pat. No. 7,291,462), Golub et al. (U.S. Pat. No. 6,949,342), Ogden et al. (U.S. Pat. No. 6,841,350), An et al. (U.S. Pat. No. 6,171,796), Bergan et al. (US 2009/0124569), Bhowmick (US 2009/0017463), Srivastava et al. (US 2008/0269157), Chinnaiyan et al. (US 2008/0222741), Thaxton et al. (US 2008/0181850), Dahary et al. (US 2008/0014590), Diamandis et al. (US 2006/0269971), Rubin et al. (US 2006/0234259), Einstein et al. (US 2006/0115821), Paris et al. (US 2006/0110759), Condon-Cardo (US 2004/0053247), and Ritchie et al. (US 2009/0127454). Biomarkers associated with development of pancreatic cancer are shown in Sahin et al. (U.S. Pat. No. 7,527,933), Rataino et al. (U.S. Pat. No. 7,507,541), Schleyer et al. (U.S. Pat. No. 7,476,506), Domon et al. (U.S. Pat. No. 7,473,531), McCaffey et al. (U.S. Pat. No. 7,358,231), Price et al. (U.S. Pat. No. 7,229,770), Chan et al. (US 2005/0095611), Mitchl et al. (US 2006/0258841), and Faca et al. (PLoS Med 5(6): e123, 2008). Biomarkers associated with development of lung cancer are shown in Sahin et al. (U.S. Pat. No. 7,527,933), Hutteman (U.S. Pat. No. 7,473,530), Bae et al. (U.S. Pat. No. 7,368,255), Wang (U.S. Pat. No. 7,348,142), Nacht et al. (U.S. Pat. No. 7,332,590), Gure et al. (U.S. Pat. No. 7,314,721), Patel (U.S. Pat. No. 7,300,765), Price et al. (U.S. Pat. No. 7,229,770), O'Brien et al. (U.S. Pat. Nos. 7,291,462 and 6,316,213), Muramatsu et al. (U.S. Pat. No. 7,090,983), Carson et al. (U.S. Pat. No. 6,576,420), Giordano (U.S. Pat. No. 5,840,506), Guo (US 2009/0062144), Tsao et al. (US 2008/0176236), Nakamura et al. (US 2008/0050378), Raponi et al. (US 2006/0252057), Yip et al. (US 2006/0223127), Pollock et al. (US 2006/0046257), Moon et al. (US 2003/0224509), and Budiman et al. (US 2009/0098543). Biomarkers associated with development of skin cancer (e.g., basal cell carcinoma, squamous cell carcinoma, and melanoma) are shown in Roberts et al. (U.S. Pat. No. 6,316,208), Polsky (U.S. Pat. No. 7,442,507), Price et al. (U.S. Pat. No. 7,229,770), Genetta (U.S. Pat. No. 7,078,180), Carson et al. (U.S. Pat. No. 6,576,420), Moses et al. (US 2008/0286811), Moses et al. (US 2008/0268473), Dooley et al. (US 2003/0232356), Chang et al. (US 2008/0274908), Alani et al. (US 2008/0118462), Wang (US 2007/0154889), and Zetter et al. (US 2008/0064047). Biomarkers associated with development of multiple myeloma are shown in Coignet (U.S. Pat. No. 7,449,303), Shaughnessy et al. (U.S. Pat. No. 7,308,364), Seshi (U.S. Pat. No. 7,049,072), and Shaughnessy et al. (US 2008/0293578, US 2008/0234139, and US 2008/0234138). Biomarkers associated with development of leukemia are shown in Ando et al. (U.S. Pat. No. 7,479,371), Coignet (U.S. Pat. Nos. 7,479,370 and 7,449,303), Davi et al. (U.S. Pat. No. 7,416,851), Chiorazzi (U.S. Pat. No. 7,316,906), Seshi (U.S. Pat. No. 7,049,072), Van Baren et al. (U.S. Pat. No. 6,130,052), Taniguchi (U.S. Pat. No. 5,643,729), Insel et al. (US 2009/0131353), and Van Bockstaele et al. (Blood Rev. 23(1):25-47, 2009). Biomarkers associated with development of lymphoma are shown in Ando et al. (U.S. Pat. No. 7,479,371), Levy et al. (U.S. Pat. No. 7,332,280), and Arnold (U.S. Pat. No. 5,858,655). Biomarkers associated with development of bladder cancer are shown in Price et al. (U.S. Pat. No. 7,229,770), Orntoft (U.S. Pat. No. 6,936,417), Haak-Frendscho et al. (U.S. Pat. No. 6,008,003), Feinstein et al. (U.S. Pat. No. 6,998,232), Elting et al. (US 2008/0311604), and Wewer et al. (2009/0029372). The content of each of the above references is incorporated by reference herein in its entirety.

Incorporation By Reference

References and citations to other documents, such as patents, patent applications, patent publications, journals, books, papers, web contents, have been made throughout this disclosure. All such documents are hereby incorporated herein by reference in their entirety for all purposes.

Equivalents

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A method of detecting multiple analytes in a sample, the method comprising the steps of:
   obtaining a sample comprising at least one target nucleic acid and at least one target protein;
   introducing an aptamer that binds to the target protein in the sample;
   removing unbound aptamer; and
   conducting a single assay, wherein the assay detects both the target nucleic acid and the target protein, the assay comprising: performing a sequencing reaction on the target nucleic acid and the aptamer, wherein sequencing comprises: hybridizing a primer to each of the nucleic acid and the aptamer to form each of a nucleic acid/primer duplex and an aptamer/primer duplex; contacting each of the duplexes with a polymerase enzyme in the presence of at least one detectably labeled nucleotide under conditions that permit the polymerase to add nucleotides to the primers in a template-dependent manner; detecting a signal from the incorporated labeled nucleotide; and sequentially repeating the contacting and detecting steps at least once, wherein sequential detection of incorporated labeled nucleotide determines the sequence of each of the nucleic acid and the aptamer thereby detecting the nucleic acid and the aptamer in the sample.

2. The method according to claim 1, further comprising quantifying the target nucleic acid.

3. The method according to claim 1, further comprising quantifying the target protein.

4. The method according to claim 1, further comprising quantifying the target nucleic acid and the target protein.

5. The method according to claim 1, wherein prior to sequencing, the nucleic acid and the aptamer are attached to a substrate.

6. The method according to claim 5, wherein the nucleic acid and the aptamer are directly attached to the substrate.

7. The method according to claim 5, wherein the nucleic acid and the aptamer are indirectly attached to the substrate.

8. The method according to claim 1, wherein prior to sequencing, the method further comprises amplifying the nucleic acid.

9. The method according to claim 1, wherein sequencing is sequencing by synthesis.

10. The method according to claim 9, wherein the sequencing by synthesis is single molecule sequencing by synthesis.

11. The method according to claim 1, wherein the detectably labeled nucleotide is an optically labeled nucleotide.

12. The method according to claim 11, wherein the optically labeled nucleotide is a fluorescently labeled nucleotides.

13. The method according to claim 1, wherein the target nucleic acid is associated with a disease.

14. The method according to claim 13, wherein the disease is cancer.

15. The method according to claim 13, wherein the target nucleic acid is selected from the group consisting of: FGFR3, K-ras, K-ras2, APC, DCC, TP53, PRC1, NUSAPI1, CAPZ, PFKP, EVER1, FLT1, ESPL1, AKAP2, CDC45L, RAMP, SYNGR2, NDRG1, ZNF533, and hypermethylated nucleic acid.

16. The method according to claim 1, wherein the target protein is associated with a disease.

17. The method according to claim 16, wherein the disease is cancer.

18. The method according to claim 17, wherein the target protein is selected from the group consisting of: MMP-2, MMP-9, MMP9/NGAL complex, MMP/TIMP complex, MMP/TIMP1 complex, ADAMTS-7, ADAM-12, thymosin 15, thymosin 16, profilin, prohibitin, ubiquitin, tropomyosin, Cyr61, cystatin B, and chaperonin 10.

19. A method for diagnosing a disease, the method comprising:
   obtaining a sample comprising at least one target nucleic acid and at least one target protein, each of which is suspected of being associated with a disease;
   introducing an aptamer that binds to the target protein in the sample;
   removing unbound aptamer;
   conducting a single assay, wherein the assay detects both the target nucleic acid and the target protein, the assay comprising: performing a sequencing reaction on the target nucleic acid and the aptamer; wherein sequencing comprises: hybridizing a primer to each of the nucleic acid and the aptamer to form each of a nucleic acid/primer duplex and an aptamer/primer duplex; contacting each of the duplexes with a polymerase enzyme in the presence of at least one detectably labeled nucleotide under conditions that permit the polymerase to add nucleotides to the primers in a template-dependent manner; detecting a signal from the incorporated labeled nucleotide; and sequentially repeating the contacting and detecting steps at least once, wherein sequential detection of incorporated labeled nucleotide determines the sequence of each of the nucleic acid and the aptamer; and
   diagnosing the disease based on results of the assay.

20. A method for diagnosing a cancer, the method comprising:
   obtaining a sample comprising at least one target nucleic acid and at least one target protein, each of which is suspected of being associated with a cancer;
   introducing an aptamer that binds to the target protein in the sample;
   removing unbound aptamer;
   conducting a single assay, wherein the assay detects both the target nucleic acid and the target protein, the assay comprising: performing a sequencing reaction on the target nucleic acid and the aptamer; wherein sequencing comprises: hybridizing a primer to each of the nucleic acid and the aptamer to form each of a nucleic acid/primer duplex and an aptamer/primer duplex; contacting each of the duplexes with a polymerase enzyme in the presence of at least one detectably labeled nucleotide under conditions that permit the polymerase to add nucleotides to the primers in a template-dependent manner; detecting a signal from the incorporated labeled nucleotide; and sequentially repeating the contacting and detecting steps at least once, wherein sequential detection of incorporated labeled nucleotide determines the sequence of each of the nucleic acid and the aptamer; and
   diagnosing the cancer based on results of the assay.

21. The method according to claim 20, wherein the cancer is bladder or colorectal cancer.

\* \* \* \* \*